US010330585B2

(12) United States Patent
Koseki et al.

(10) Patent No.: US 10,330,585 B2
(45) Date of Patent: Jun. 25, 2019

(54) DEVICE FOR COUNTING (71) Applicant: TOYO SEIKAN GROUP HOLDINGS, LTD., Tokyo (JP)

(72) Inventors: Osamu Koseki, Tokyo (JP); Ryo Suenaga, Kanagawa (JP); Masahiro Kuninori, Kanagawa (JP)

(73) Assignee: TOYO SEIKAN GROUP HOLDINGS, LTD., Tokyo (JP)

( * ) Notice: Subject to any disclaimer, the term of this patent is extended or adjusted under 35 U.S.C. 154(b) by 3 days.

(21) Appl. No.: 14/976,705

(22) Filed: Dec. 21, 2015

(65) Prior Publication Data

US 2016/0109354 A1 Apr. 21, 2016

Related U.S. Application Data (63) Continuation of application No. PCT/JP2014/003330, filed on Jun. 20, 2014.

(30) Foreign Application Priority Data

Jul. 9, 2013 (JP) .................................. 2013-143745

(51) Int. Cl.
*C12M 1/32* (2006.01)
*G01N 33/96* (2006.01)
(Continued)

(52) U.S. Cl.
CPC ......... *G01N 15/1463* (2013.01); *C12M 41/36* (2013.01); *G01N 15/06* (2013.01);
(Continued)

(58) Field of Classification Search
USPC ............... 422/73; 436/10; 435/3, 29–34, 39, 435/289.1, 292.1, 293.1, 293.2, 294.1,
(Continued)

(56) References Cited

U.S. PATENT DOCUMENTS 7,547,540 B2 * 6/2009 Takagi ................... C12M 35/04
435/289.1
2006/0097155 A1 * 5/2006 Adachi ............. B01L 3/502784
250/288
(Continued)

FOREIGN PATENT DOCUMENTS

EP       3045521 A1    7/2016
JP    2004-323077 A   11/2004
(Continued)

OTHER PUBLICATIONS

International Search Report issued in corresponding International Application No. PCT/JP2014/003330 dated Sep. 22, 2014 (3 pages).
(Continued)

*Primary Examiner* — Dean Kwak
(74) *Attorney, Agent, or Firm* — Osha Liang LLP (57) ABSTRACT

A counting device counts the number of counting objects in liquid in a flexible container. The counting device includes a mounting table on which the container is mounted and a pressing table arranged opposite to a container-arranged side of the mounting table. The mounting table and the pressing table move relatively in a direction of sandwiching the container, and a light-passing hole facing a surface of the container is provided in at least one of the mounting table and the pressing table. The pressing table includes one or more thickness-setting members that sandwich the container between the pressing table and the mounting table in a periphery of the light-passing hole and on the side opposite to the container in a protruding manner.

5 Claims, 9 Drawing Sheets

(51) Int. Cl.
*G01N 15/14* (2006.01)
*C12M 1/34* (2006.01)
*G01N 33/48* (2006.01)
*G01N 15/06* (2006.01)
*G01N 15/10* (2006.01)
*G01N 15/00* (2006.01)

(52) U.S. Cl.
CPC ..... *G01N 33/48* (2013.01); *G01N 2015/0065* (2013.01); *G01N 2015/0693* (2013.01); *G01N 2015/1006* (2013.01); *G01N 2015/1486* (2013.01)

(58) Field of Classification Search
USPC ............................... 435/297.5, 298.1, 299.1
See application file for complete search history.

(56) References Cited

U.S. PATENT DOCUMENTS

| | | | | |
|---|---|---|---|---|
| 2009/0141345 | A1* | 6/2009 | Tsuchiya | B01L 9/523 359/393 |
| 2010/0075406 | A1* | 3/2010 | Tanaka | C12M 23/14 435/287.1 |
| 2011/0124114 | A1* | 5/2011 | Ermantraut | B01L 3/50273 436/164 |
| 2011/0318725 | A1* | 12/2011 | Suenaga | C12M 23/14 435/3 |
| 2014/0011186 | A1 | 1/2014 | Suenaga et al. | |

FOREIGN PATENT DOCUMENTS

| | | |
|---|---|---|
| JP | 2007-322685 A | 12/2007 |
| JP | 2011-087498 A | 5/2011 |
| JP | 2012-044872 A | 3/2012 |
| WO | 99/43790 A1 | 9/1999 |
| WO | 2011/107102 A1 | 9/2011 |

OTHER PUBLICATIONS

Written Opinion of the International Searching Authority issued in PCT/JP2014/003330 dated Sep. 22, 2014 (4 pages).

Extended European Search Report issued in corresponding European Patent Application No. 14823779.5 dated Jan. 31, 2017 (7 pages).

* cited by examiner

| H(mm) | W1(mm) | | |
|---|---|---|---|
| | 500ml | 1000ml | 1500ml |
| 0 | 0 | 0 | 0 |
| 0.6 | 6 | 4 | 5 |
| 1.1 | 9 | 8 | 8 |
| 1.6 | 11 | 12 | 9 |
| 2.1 | 14 | 14 | 11 |
| 2.6 | 16 | 16 | 14 |
| 3.2 | 18 | 18 | 16 |
| 4.2 | 22 | 23 | 18 |

| Block gap(mm) | Measurement-possible region(mm) |
|---|---|
| 30 | 20 |
| 20 | 10 |
| 15 | 5 |
| 10 | 0 |

DEVICE FOR COUNTING

TECHNICAL FIELD

The present invention relates to a counting device. In particular, the present invention relates to a counting device for counting the number of cells in culture liquid in a sealed culture container.

BACKGROUND ART

In recent years, in the fields of production of medicines, gene therapy, regenerative medicine, immunotherapy or the like, it is required to culture a large amount of cells, tissues, microorganisms or the like efficiently in an artificial environment.

In such cell culture, in accordance with proliferation of cells, it is required to keep the density of cells in culture liquid in an appropriate range.

Specifically, if the density of cells in culture liquid becomes too high, it becomes impossible to supply sufficient oxygen or nutrition to each cell, thus leading to lowering in cell proliferation efficiency. Further, if the density of cells in culture liquid is too low, a sufficient proliferation efficiency cannot be obtained.

Therefore, in cell culture, in order to grasp the density of cells during culture, it is required to count the number of cells in culture liquid in a culture container, if necessary.

For example, Patent Document 1 discloses a counting device for counting the number of counting objects in liquid in a sealed container, which is provided with a table for mounting a container thereon and an adjustment member that adjusts at least part in a container, including a measurement-possible region, to a prescribed thickness.

This counting device is further provided with an imaging means for acquiring an image of counting objects in the container; a counting means for counting the number of the counting objects in an acquired image; and a driving means for driving the adjusting member that adjusts the thickness of at least part of the container to a prescribed thickness such that the number of the counting objects in the image will fall within a prescribed range if the number of the counting objects is not within a prescribed range as a result of measuring by means of the counting means.

Here, the principle of the method for counting the number of counting objects in Patent Document 1 will be explained with reference to FIG. 10. The principle of this counting method is applied to the counting device of one or more embodiments of the present invention.

Figure 10A:
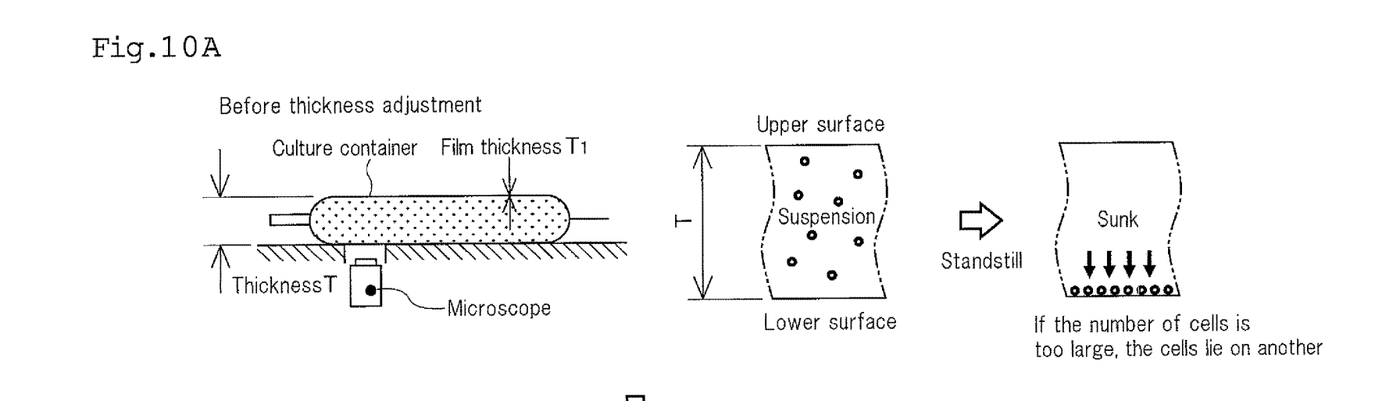
FIGS. 10A and 10B are schematic views for explaining the principle of the method for counting the number of counting objects in a container relating to the present invention.

FIG. 10 shows a state where cells in a culture container are directly observed by means of a microscope and the number of the cells is counted. FIG. 10A shows a state in which observation is conducted without adjusting the thickness T of the culture container. By using culture liquid having a specific gravity that is lower than that of cells, it becomes possible to allow cells to be sunk to the bottom of the culture container such that the cells can be those suited to microscopic observation. On the contrary, observation may be conducted by collecting cells to the upper part of the container by using culture liquid having a high specific gravity.

In the case of the state shown in FIG. 10A, as the number of cells in the culture container is increased, the cells gradually lie one on another when the cells are suspended and allowed to be settled. Therefore, by this method, the number of cells cannot be counted accurately when a large amount of cells is cultured.

Figure 10B:
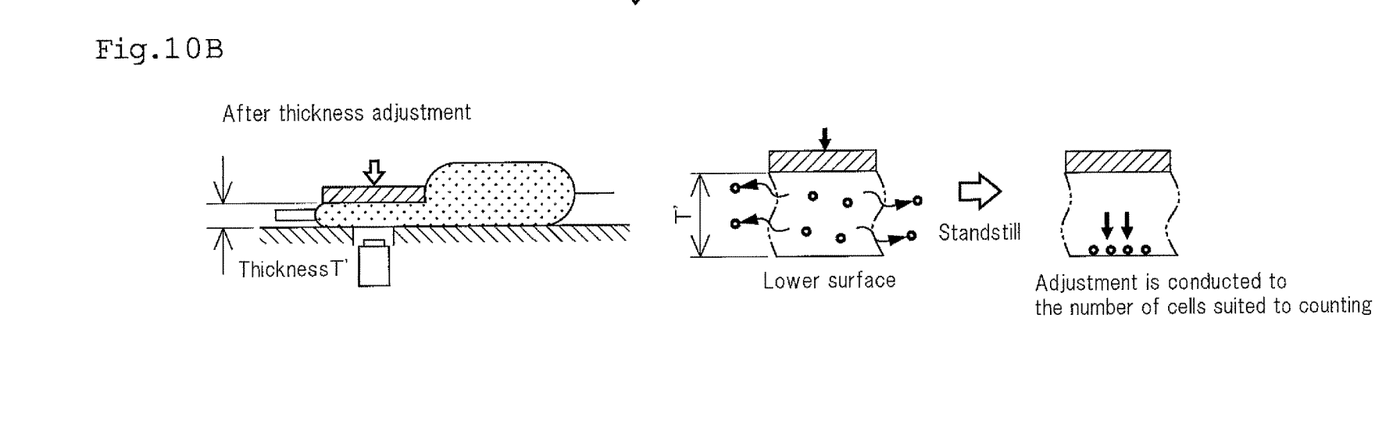

Therefore, in the counting device of the Patent Document 1, in the case where accurate counting is impossible due to excessive number of cells, as shown in FIG. 10B, by reducing the thickness of the culture container to T', the number of cells in a measurement range (observation range) is reduced, whereby the number of cells is adjusted to the number suited to counting.

As a result, if a large amount of cells is cultured in a culture container, by observing cells in a culture container directly, the number of cells can be counted without opening the culture system.

Further, when the number of cells in a culture container is small, and prediction of density of cells in an entire culture container is difficult, by increasing the thickness of a culture container, the number of cells in an observation range is increased, whereby the number of cells in the observation range can be adjusted to that suited to counting.

RELATED ART DOCUMENT

Patent Document

Patent Document 1: JP-A-2011-87498

SUMMARY OF THE INVENTION

However, although the counting device disclosed in Patent Document 1 is capable of counting cells in a culture container without opening the culture system irrespective of the density of cells, the thickness-adjusting means adjusts at least part including a range to be measured in the container (also called "measurement-possible region") to a prescribed thickness, i.e. as a prescribed thickness as the total sum of the liquid thickness and the film thickness. Therefore, if the film thicknesses $T_1$ of the containers (see FIG. 10) vary, the volume of a liquid in the measurement-possible region increases or decreases in accordance with such variation in film thickness, and the accuracy of the measurement may be lowered when the density of cells is calculated. In addition, if containers differing in film thickness are erroneously used, incorrect density of cells may be calculated.

Further, when containers differing in film thickness are used, the thickness is required to be adjusted taking into consideration the film thickness of each container. Therefore, labor required for this adjustment has been desired to be reduced or eliminated, thus leading to improvement in workability and reliability.

In one aspect, the present invention provides a counting device capable of improving measurement accuracy, workability and reliability.

The counting device of one or more embodiments of the present invention is a counting device for counting the number of counting objects in liquid in a flexible container, wherein the device is provided with a mounting table for mounting the container thereon and a pressing table being arranged so as to oppose to the container-arranged side of the mounting table;

the mounting table and the pressing table are capable of moving relatively in a direction of sandwiching the container, and a light-passing hole facing the surface of the container is provided in at least one of the mounting table and the pressing table; and the pressing table is provided with one or plural thickness-setting members sandwiching the container between the pressing table and the mounting table in the periphery of the light-passing hole and on the side opposite to the container in a protruding manner.

Advantageous Effects of the Invention

According to one or more embodiments of the present invention, if the film thicknesses of the containers vary, measurement can be conducted without taking such variations into consideration. As a result, a disadvantage that the accuracy of measurement such as the density of cells is lowered can be prevented. Further, if containers differing in film thickness are used, since there is no need to take into consideration the film thickness of each container, workability and reliability can be improved.

In addition, since there is no need to take the liquid out of the container, risk of contamination can be eliminated when the liquid is culture liquid. Further, a measurer is not required to be skilled, and objective data can be obtained.

DETAILED DESCRIPTION OF THE INVENTION

Hereinbelow, one or more embodiments of the present invention will be explained in detail.

Figure 1:
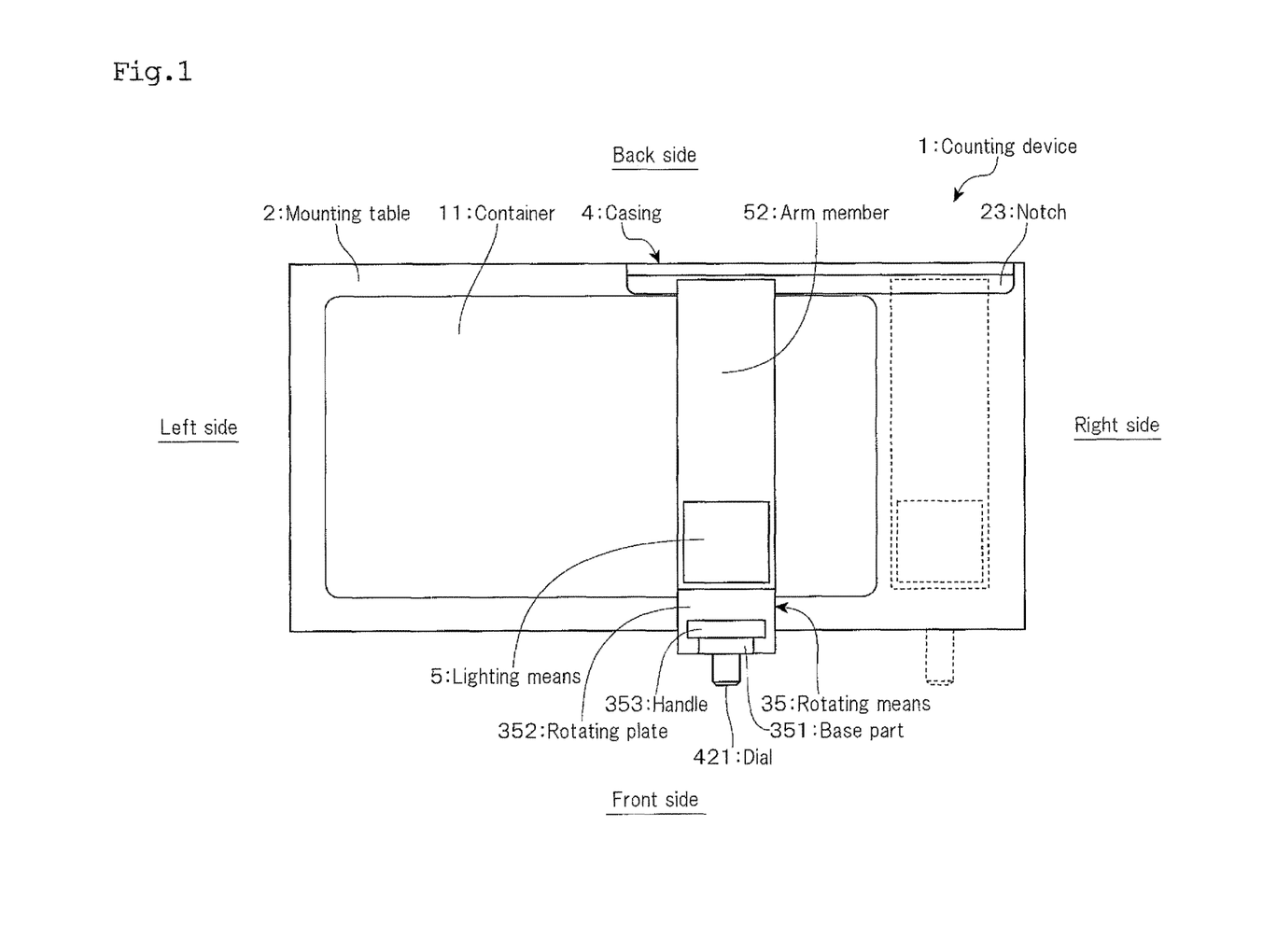
FIG. 1 is a schematic plan view of a counting device according to one or more embodiments of the present invention.
Figure 2:
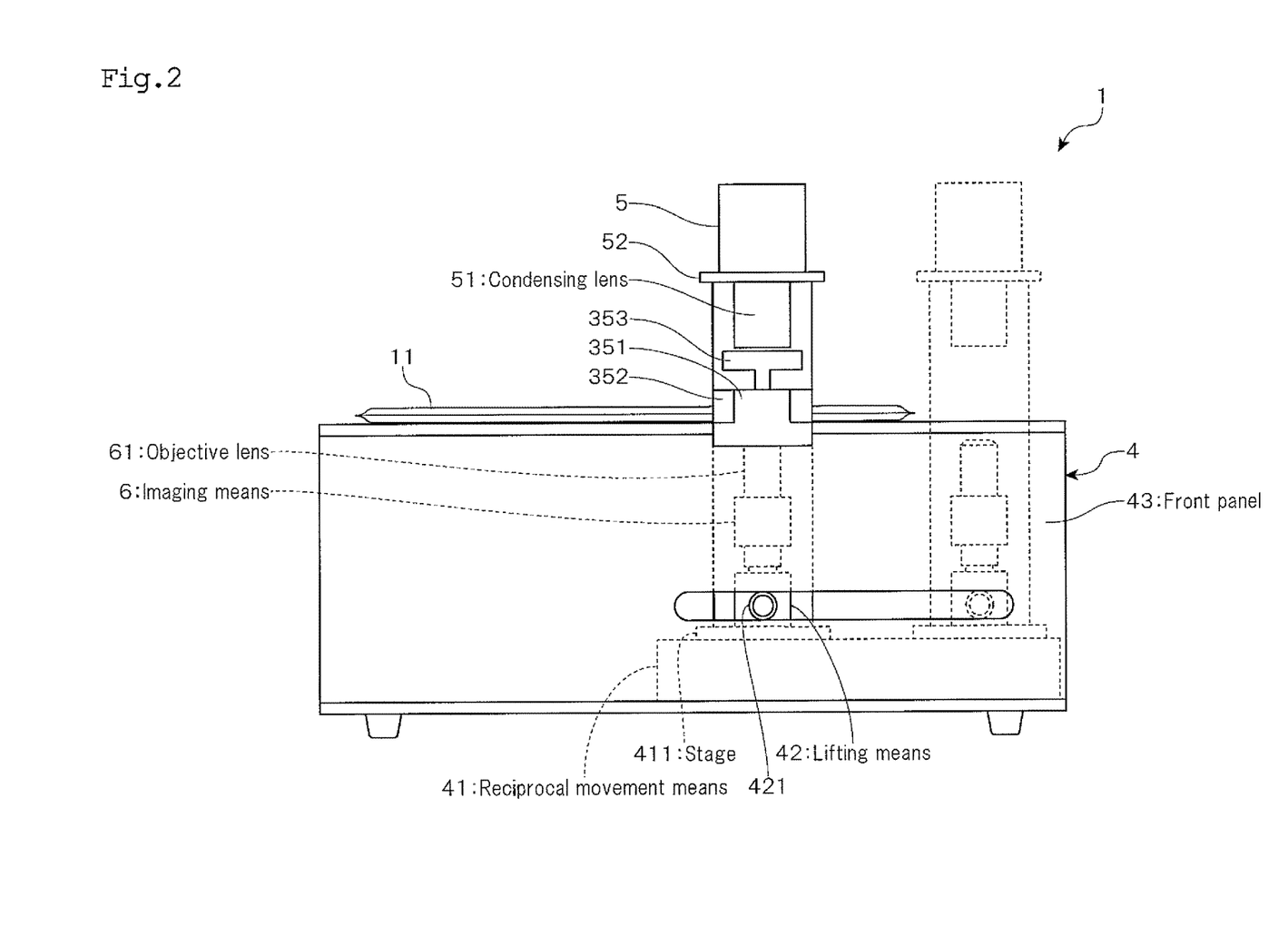
FIG. 2 is a schematic front elevation view of the counting device according to one or more embodiments of the present invention.
Figure 3:
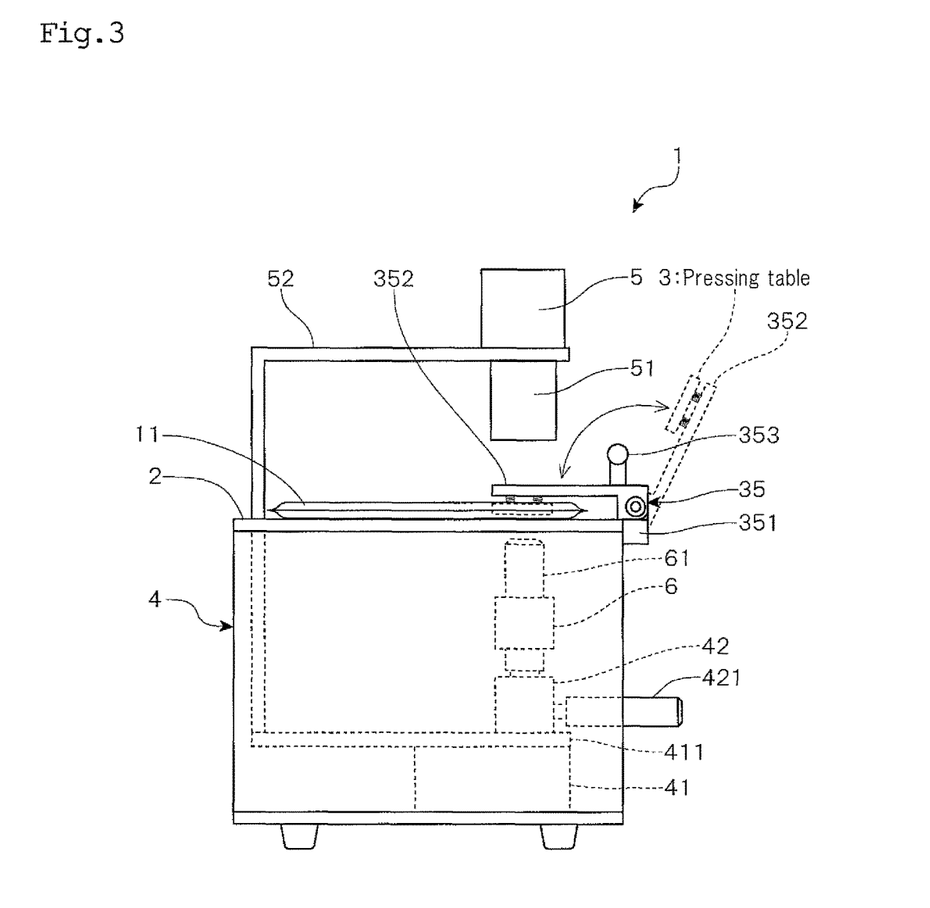
FIG. 3 is a schematic left lateral view of the counting device according to one or more embodiments of the present invention.

In FIGS. 1 to 3, a counting device 1 is provided with a mounting table 2, a pressing table 3, a casing 4, a lightening means 5, an imaging means 6 or the like. It counts the number of counting objects in liquid in the container 11 having flexibility.

In one or more embodiments, the container 11 is an almost transparent culture container that is formed of a resin. Culture liquid 10 is sealed in the container 11, and the counting objects are cells.

(Container)

The container 11 is a container in the form of a bag obtained by using a soft packaging material. By using a soft packaging material as the material of the container 11, it is possible to impart flexibility and softness to the container 11. As the soft packaging material, for example, one disclosed in JP-A-2004-323077 (pressurized bag-shaped container for pouring) or the like can be used.

The container 11 has gas permeability that is required for cell culture. In order to allow contents to be confirmed visibly, one or entire thereof has transparency. As the material for the culture container satisfying such conditions, for example, polyolefin, ethylene-vinyl acetate copolymer, styrene-based elastomer, polyester-based thermoplastic elastomer, silicone-based thermoplastic elastomer, silicone rubber or the like can be given.

(Mounting Table)

Figure 4A:
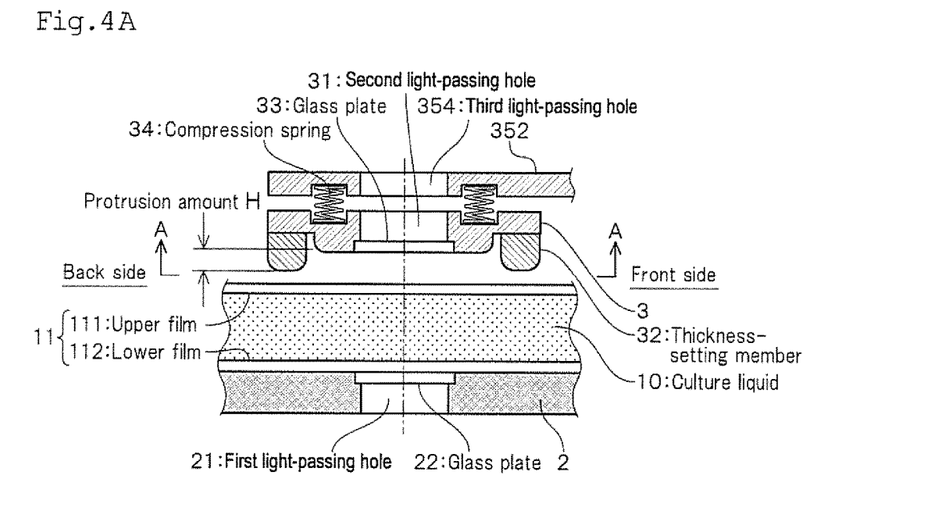
FIGS. 4A-4C are schematic views of essential parts of the counting device according to one or more embodiments of the present invention, in which 4A is an enlarged cross-sectional view, 4B is a fragmentary view taken in the direction of the arrow A-A, and 4C is an enlarged cross-sectional view during counting.
Figure 4B:
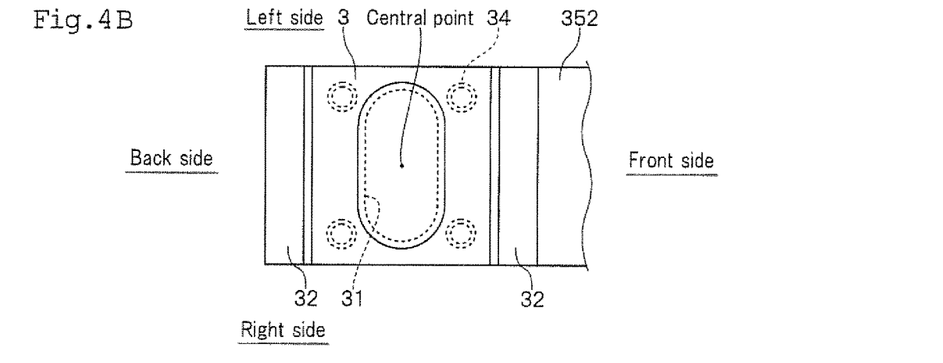
Figure 4C:
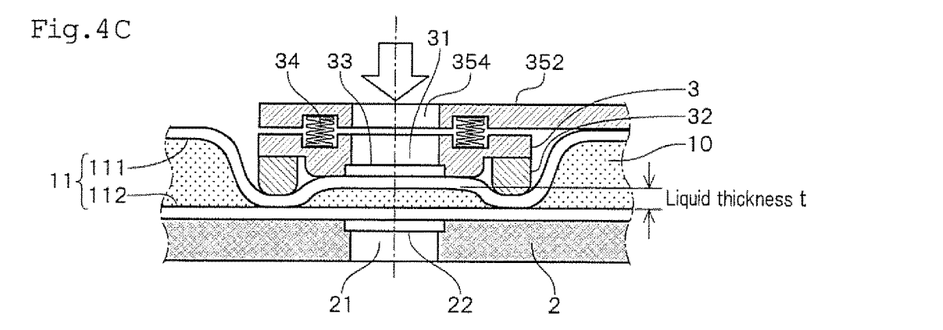

The mounting table 2 is an almost rectangular flat plate, and is provided on the top of an almost rectangular parallelepiped casing 4. On the upper surface thereof, the container 11 is mounted. As shown in FIG. 4C, in the mounting table 2, a first light-passing hole 21 is formed below a second light-passing hole 31 of the pressing table 3. To the upper part of the first light-passing hole 21, a flat glass plate 22 is attached. The first light-passing hole 21 has an almost ellipsoidal shape and, further, in the mounting table 2, on the edge part on the backside on the right, a notch 23 for allowing an arm member 52 to movably pass therethrough is formed. The first light-passing hole 21 is provided to face the surface (lower surface) of the container 11.

In one or more embodiments, the first light-passing hole 21 serves as a hole for acquiring an image of cells in the container 11 by the imaging means 6 accommodated in the casing 4. Further, the glass plate 22 is transparent in order to acquire an image of the container 11. Further, the upper surface of the glass plate 22 is on the same plane as the upper surface of the mounting table 2, and supports the container 11.

The configuration is not limited thereto, and a part through which light passes (not shown) may be provided instead of the first light-passing hole 21. That is, if at least part of the mounting table 2 is formed of a transparent element (for example, an acrylic plate), the transparent member serves as the part through which light passes, and hence the first light-passing hole 21 and the glass plate 22 may not necessarily be provided.

(Pressing Table)

The pressing table 3 has a second light-passing hole 31 that faces the surface (upper surface) of the container 11. In the periphery of the second light-passing hole 31 and on the side opposite to the container 11, the thickness-setting member 32 that sandwiches the container 11 between the pressing table 3 and the mounting table 2 is provided in a protruding manner.

That is, the pressing table 3 is an almost rectangular flat plate, and the pressing table 3 is arranged such that it opposes to the container 11-arranged side of the mounting table 2 (i.e. above the mounting table 2). As shown in FIG.

4, as for this pressing table 3, almost square bar-like thickness-setting members 32 are independently connected to the edge part on the front side and the edge part on the back side. In this thickness-setting member 32, the upper surface as one of side surfaces is connected with the lower surface of the pressing table 3, and the lower surface as one of side surfaces is protruded downwardly in a protrusion amount of H from the glass plate 33 of the pressing table 3. As for the relationship between the protrusion amount H and the liquid thickness t, and the relationship between the protrusion amount H and the measurement-possible region will be mentioned later.

In almost center of the pressing table 3, the second light-passing hole 31 is formed. Below the second light-passing hole 31, a flat glass plate 33 is attached. The second light-passing hole 31 is almost elliptical, and the longitudinal direction of the ellipsoid is in parallel with the crosswise direction of the counting device 1.

In one or more embodiments, the second light-passing hole 31 is a hole for allowing the container 11 to be irradiated with light emitted from the lighting means 5. Further, the glass plate 33 is transparent in order for light to be irradiated therethrough. The lower surface of the glass plate 33 is on the same plane as the lower surface of the pressing table 3, and presses down the container 11.

However, the present invention is not limited to the above-mentioned configuration. Instead of the second light-passing hole 31, a transparent part (not shown) may be provided. That is, when at least part of the pressing table 3 is formed of a transparent member (an acrylic plate, for example), the transparent member serves as the part through which light passes, and there is no need to provide the second light-passing hole 31 and the glass plate 33.

This pressing table 3 is attached to a rotating plate 352 of a rotating means 35.

This rotating means 35 is provided with a base part 351 that is fixed to the end part on the front side of the mounting table 2, an almost rectangular rotating plate 352 that is pivotably supported by the base part 351 and in which a third light-passing hole 354 is formed, a handle 353 that is attached to this rotating plate 352 and a locking mechanism (not shown) that keeps the state in which the pressing table 3 presses the container 11. The rotating means 35 moves the pressing table 3 in the direction of sandwiching the container 11, and keeps the state in which the container 11 is sandwiched.

In one or more embodiments, the pressing table 3 is moved by the rotating means 35. The configuration is not limited thereto. For example, although not shown, the pressing table 3 may be moved by using a lifting means.

In this configuration, the mounting table 2 is not moved, and the pressing table 3 is moved. The configuration is not limited thereto. It suffices that the mounting table 2 and the pressing table 3 are relatively moved in a direction of sandwiching the container 11.

The pressing table 3 may be provided with a pressing force-adjusting member.

In one or more embodiments, as the pressing force-adjusting member, plural compression springs 34 are provided, and the pressing table 3 is connected with the rotating plate 352 through a compression spring 34. By this configuration, the following disadvantages can be prevented without fail; when the container 11 is sandwiched between the mounting table 2 and the pressing table 3, the thickness-setting member 32 pushes the container 11 too strongly, thereby causing damage to the container 11 or the thickness-setting member 32 does not press the container 11 sufficiently, and as a result, a part of an upper film 111 of the container 11 that is pressed down by the thickness-setting member 32 is floated for a minor distance from the lower film 112 of the container 11.

The state that the container 11 is sandwiched between the mounting table 2 and the pressing table 3 means a state in which a part of the upper film 111 of the container 11 that is pressed down by the thickness-setting member 32 is brought into contact with a part of the lower film 112 of the container 11.

Further, the thickness-setting member 32 may be protruded in the pressing table 3 in a manner that the protrusion amount is adjustable. In this way, as mentioned later, due to the relationship of the protrusion amount H=liquid thickness t, the liquid thickness t can be adjusted easily.

Although not shown, the adjustment of the protrusion amount can be conducted by means of a screw, a cam, a ratchet wrench or the like. Further, pressing tables 3 differing in protrusion amount are prepared in advance, and the pressing tables 3 may be exchanged.

(Lighting Means)

The lighting means 5 is provided with a light source (not shown) such as LED, a condensing lens 51 or the like, and emits light to a measurement-possible region in the container 11 through the third light-passing hole 354, the second light-passing hole 31 and the glass plate 33, and provides brightness required for acquiring an image of cells by means of an imaging means 6.

The lighting means 5 is attached to a stage 411 of a reciprocal movement means 41 through an arm member 52 and is capable of moving in the crosswise direction. As a result, workability or the like when the container 11 is placed on the mounting table 2 can be improved.

(Imaging Means)

The imaging means 6 is a CCD camera and has an objective lens 61 for acquiring an image in an enlarged mode. The imaging means 6 acquires an image of cells (not shown) in the culture liquid 10. This imaging means 6 is attached to the stage 411 of the reciprocal movement means 41 through a lifting means 42, and can move in the crosswise direction.

(Lifting Means)

The lifting means 42 is operated by means of a feed screw. A measurer rotates a dial 421 while watching an image, and allows the imaging means 6 to move up and down, thereby to adjust the focal point. Feeding of a screw is conducted not only manually but may be conducted electrically. In the case of electrical feeding, in addition to conducting adjustment of a focal point visually, automatic focal point adjustment (auto focus) can be used.

(Reciprocal Movement Means)

The reciprocal movement means 41 is an electrical actuator, is accommodated within the casing 4, and moves the lighting means 5, the imaging means 6 or the like in the crosswise direction. An electrical actuator is used as the reciprocal movement means 41, but the configuration is not limited thereto.

(Information Processing Means)

The counting device 1 is provided with an information processing means (not shown) such as a computer. This information processing means processes an image acquired by the imaging means 6, and the number of counting objects is counted. Further, this information processing means can calculate the density of cells, or the like.

(Thickness-Setting Member)

The pressing table 3 of one or more embodiments has a pair of thickness-setting members 32 as mentioned above.

Here, a pair of thickness-setting members 32 may be provided in a protruding manner at symmetrical positions relative to the central point of the second light-passing hole 31 or a horizontally-directed virtual central line (not shown) that passes this central point. The pair of thickness-setting members 32 are provided such that they are apart from each other for a prescribed distance (also called "block gap"). Therefore, when the pressing table 3 presses the container 11 down, a space is formed between the upper film 111 and the lower film 112. That is, when the pressing table 3 presses the container 11 down, culture liquid 10 below the pressing table 3 moves smoothly through the above-mentioned space.

The shape, number (in one or more embodiments, plural), arrangement or the like of the thickness-setting member 32 are not limited to those mentioned above, and can be arbitrarily set. For example, although not shown, the number of the thickness-setting member 32 may be one and the shape thereof may be "U" as viewed from the surface direction. Alternatively, the number of the thickness-setting member 32 may be one, and the shape thereof may be in the form of a ring as viewed from the surface direction and a notch may be provided at the bottom of the ring-like wall part in order to allow the culture liquid 10 to pass therethrough.

Here, the thickness-setting member 32 may satisfy conditions that it is provided in a protruding manner at symmetrical positions relative to the central point of the light-passing hole of the pressing table 3 or a horizontal virtual central line that passes this central point such that a gap is provided therebetween.

Further, when the pressing table 3 presses down the container 11, as shown in FIG. 4C, the thickness-setting member 32 pushes down the upper film 111 of the container 11, and a part of the upper film 111 that has been pushed down abuts the lower film 112. Further, a part of the upper film 111 that is positioned below the central part of the pressing table 3 is brought into contact with the glass plate 33 and the lower surface of the pressing table 3 due to the pressure of the culture liquid 10 and the flexibility of the container 11 (that is, the upper film 111).

Here, when the upper film 111 is brought into contact with the lower surface of the glass plate 33 (see FIG. 4C), the liquid thickness t below the glass plate 33 becomes equal to the protrusion amount H of the thickness-setting member 32 (see FIG. 4A, protrusion amount H=liquid thickness t). However, between a part of the upper film 111 that contacts the thickness-setting member 32 and a part of the upper film 111 that contacts the glass plate 33, the upper film 111 is deformed in an almost S-shape, and the liquid thickness t does not become equal to the protrusion amount H. Therefore, it is required to set a range that satisfies protrusion amount H=liquid thickness t as the measurement-possible region.

The range that satisfies protrusion amount H=liquid thickness t varies depending on the flexibility, the thickness of the upper film 111, the volume of the culture liquid 10 in the container 11, the protrusion amount H of the thickness-setting member 32 or the like. The inventors made intensive studies and conducted experiments, and set a range that satisfies protrusion amount H=liquid thickness t.

Next, experiments 1 and 2 regarding the range that satisfies the protrusion amount H=liquid thickness t, and the pressing table 3 in Examples 1 to 3 that satisfies the protrusion amount H=liquid thickness t will be explained with reference to the drawings.

Experiment 1

Figure 5A:
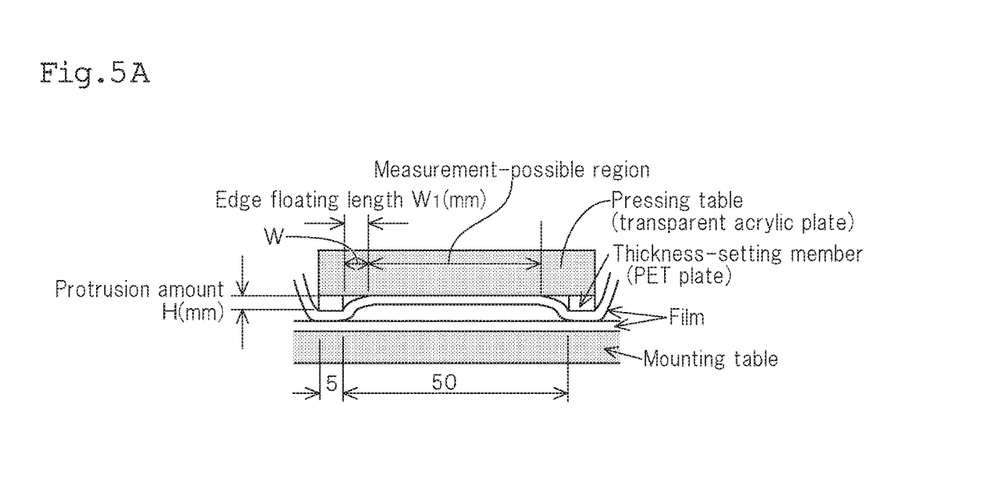
FIGS. 5A-5C are schematic views of experiment 1 for explaining a measurement-possible region of the counting device according to one or more embodiments of the present invention.
Figure 5B:
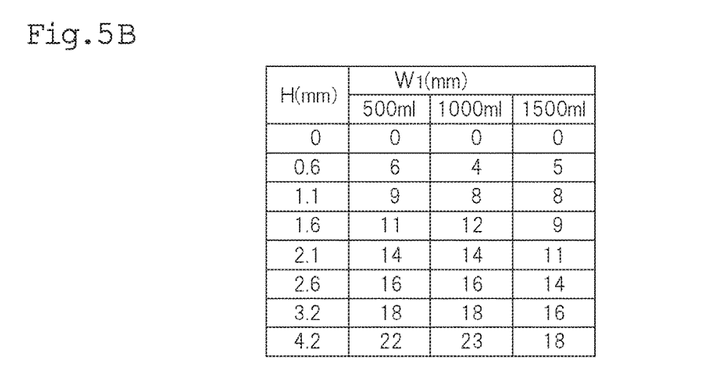
Figure 5C:
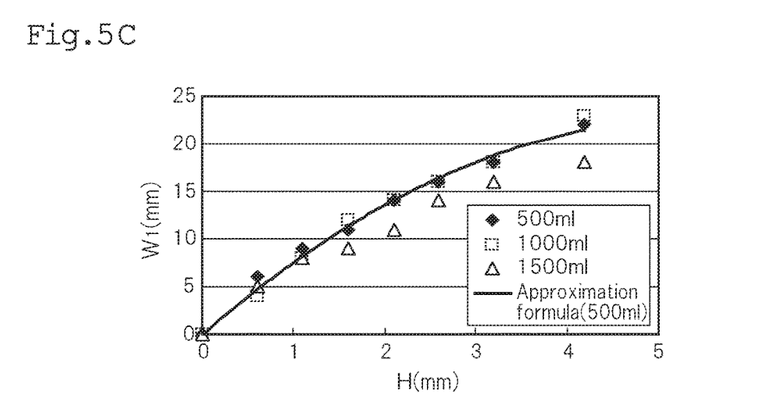

Experiment 1 was conducted as for a range that satisfies protrusion amount H=liquid thickness t.
1-1: Experiment conditions (see FIG. 5A) were as follows.
 Container (also called as a bag): a polyethylene-made bag having a thickness of 0.1 mm.
 Contents: water (water in amounts of 500 ml, 1000 ml and 1500 ml were independently sealed)
 The protrusion amount H was changed, and the center of the bag was pressed down by the pressing table, and the length $W_1$ of the film edge that had floated (hereinafter referred to as "floating length") in the vicinity of the thickness-setting member was measured.
 The measurement of the floating length $W_1$ of the film edge was conducted by visually confirming the state in which the film was in contact with the pressing table (transparent acrylic plate), and measured by means of a scale (unit: 1 mm).
1-2: The results of the experiment are shown in FIG. 5B.
1-3: As a result of the experiment in which 500 ml of water was sealed, the following approximation formula (1) of $W_1/H$ was obtained (see FIG. 5C).

$$W_1=-0.76 \times H^2+8.28 \times H \qquad \text{Approximation formula (1)}$$

Here, from the approximation formula (1), the distance W between the thickness-setting member and the measurement-possible region may be $W \geq W_1$, when the protrusion amount of the thickness-setting member is taken as H. That is, the distance W may be represented by the following formula (2).

$$W \geq -0.76 \times H^2+8.28 \times H \qquad \text{Formula (2)}$$

By this, since the upper film is brought into contact with the lower surface of the pressing table without fail, lowering in measurement accuracy can be eliminated.

Since the approximation formula (1) shows a boundary (limit), practically, the distance W may be set further inwardly by several mm (e.g. 2 to 5 mm) taking safety into consideration.

Experiment 2

Figure 6A:
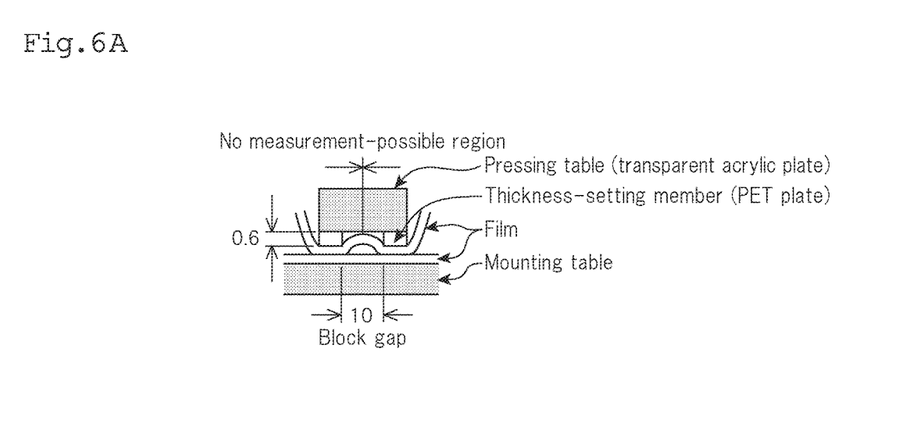
FIGS. 6A-6C are schematic views of experiment 2 for explaining a measurement-possible region of the counting device according to one or more embodiments of the present invention.

For the range that satisfies protrusion amount H=liquid thickness t, experiment 2 was conducted.
2-1: Experimental conditions (see FIG. 6A) were as follows.
 Container (also called as a bag): a polyethylene-made bag having a thickness of 0.1 mm
 Content: water (500 ml of water was sealed)
 Protrusion amount H was set to 0.6 mm, and the distance between a pair of the thickness-setting member (also called a "block gap") was varied, the center of the bag was pressed by the pressing table, whereby the measurement-possible region was measured.
 Measurement of the measurement-possible region was conducted by means of a scale (unit: 1 mm) by visually confirming the state in which the film contacts the pressing table (transparent acrylic plate).

Figure 6B:
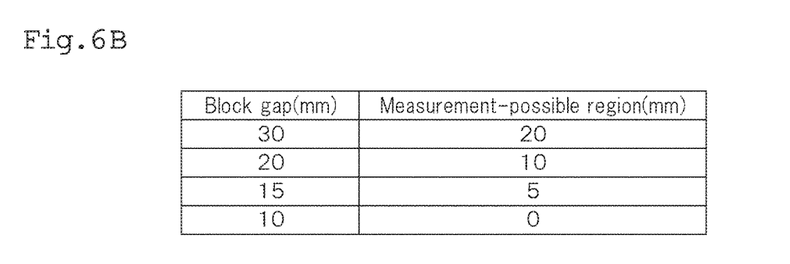
Figure 6C:
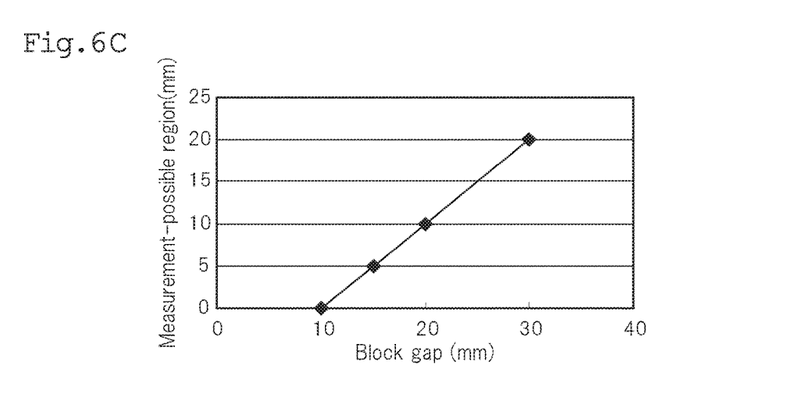

2-2: Experimental results are as shown in FIG. 6B and FIG. 6C.

2-3: When the protrusion amount H was set to 0.6 mm, if the block gap was 10 mm or less, the measurement-possible region disappeared. Therefore, when the visual field of the enlarged acquired image is 1 mm, and in order to allow the visual field that is 10 times larger than this to be a measurement-possible region, the block gap may necessarily be 20 mm or more.

According to the above-mentioned formula (2), $W_1$ becomes 14.0 mm when H=2.1 mm, and if the measurement-possible region is required to be 10 mm or more, a block gap of 14.0+10+14.0=38 mm or more is required.

Example 1

Figure 7:
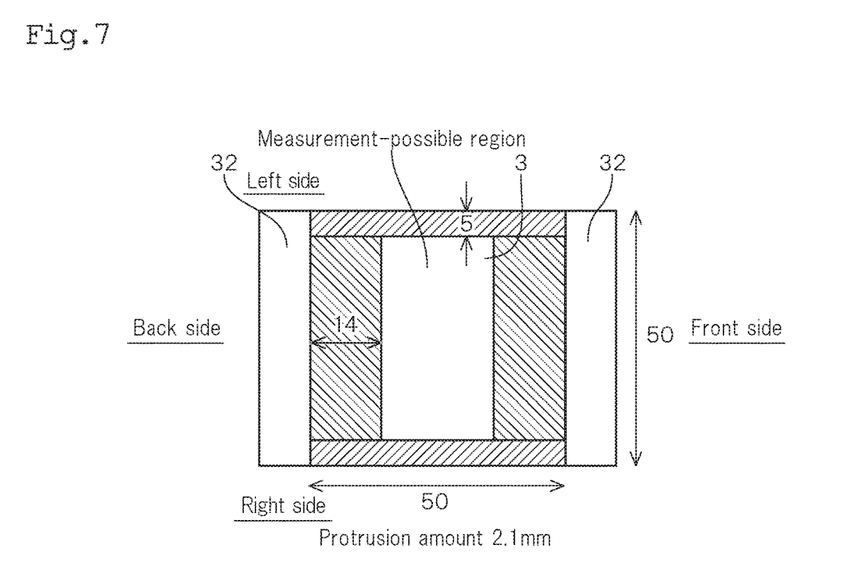
FIG. 7 is a schematic view of essential parts of the counting device for explaining a measurement-possible region of the counting device according to an example of the first embodiment of the present invention.

As shown in FIG. 7, in the pressing table 3 in Example 1, a pair of thickness-setting members 32 (the length in crosswise direction: 50 mm, the protrusion amount H=2.1 mm) were provided such that they were apart from each other for a distance of 50 mm, and the region between the pair of thickness-setting members 32 were a 50 mm×50 mm square.

In this pressing table 3, as for the measurement-possible region, in a direction connecting the front side and the back side (i.e. a direction orthogonally crossing the crosswise direction), if calculation was conducted by substituting H=2.1 mm in the above formula (2), W became 14.0 mm; that is, the measurement-possible region was positioned inwardly by 14 mm or more from the thickness-setting member 32. In the crosswise direction, the culture liquid 10 moved back and forth (reciprocal movement) at the edge part of the pressing table 3, and the measurement values were not stable. Therefore, an experiment was conducted for a distance to the position at which the measurement value became stable, and the range was found to be positioned inwardly by 5 mm or more from the left edge part and the right edge part.

The density of cells was calculated by using this pressing table 3, the density of cells was almost equal to the density of cells calculated by means of a cell counter plate.

Figure 8:
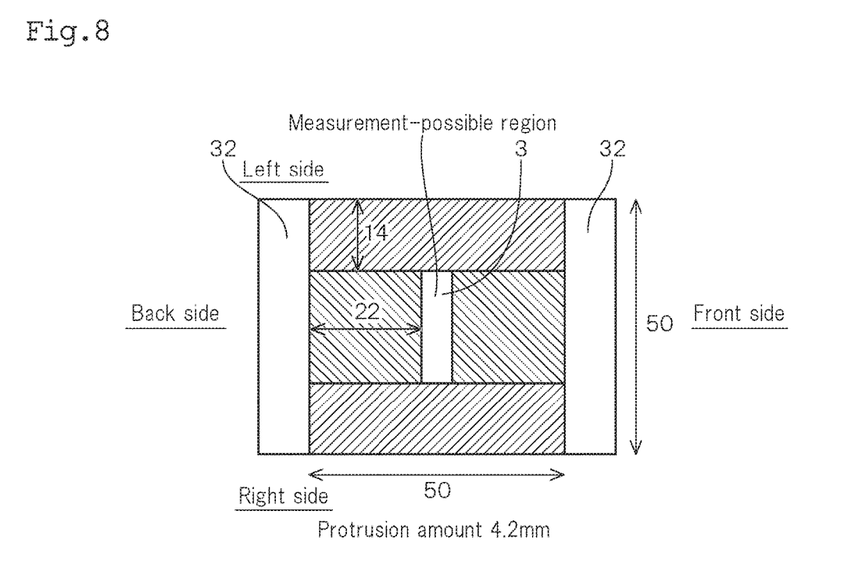
FIG. 8 is a schematic view of essential parts of the counting device for explaining a measurement-possible region of the counting device according to an example of the second embodiment of the present invention.
Figure 9:
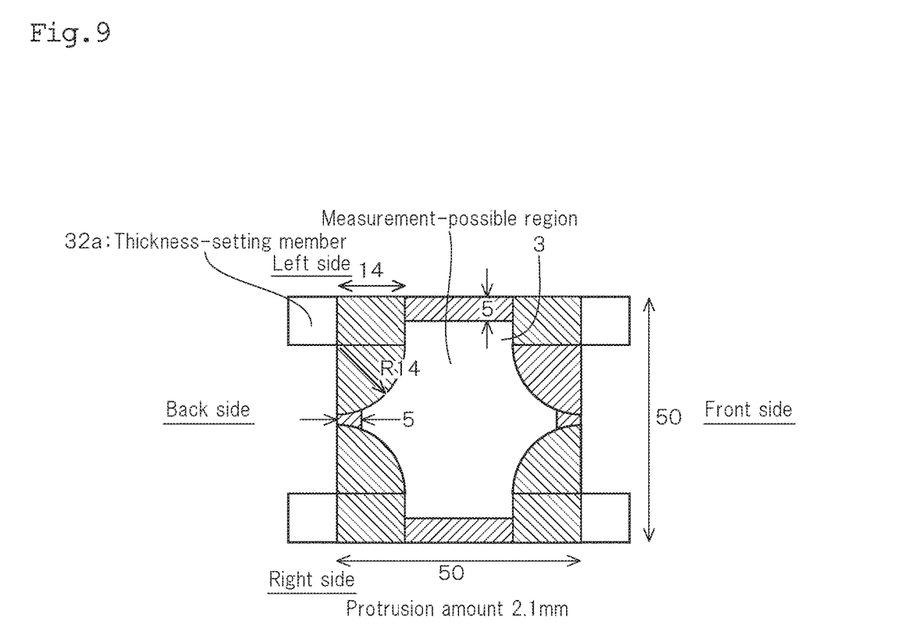
FIG. 9 is a schematic view of essential parts of the counting device for explaining a measurement-possible region of the counting device according to an example of the third embodiment of the present invention.

In FIGS. 7 to 9, a range that cannot be measured is hatched.

Example 2

As shown in FIG. 8, in the pressing table 3 in Example 2, a pair of thickness-setting members 32 (having a crosswise length of 50 mm, and a protrusion amount H of 4.2 mm) were provided in a protruding manner such that they were apart from each other for a distance of 50 mm. A region between the pair of the thickness-setting members 32 is a 50 mm×50 mm square.

In this pressing table 3, as for the measurement-possible region, in a direction connecting the front side and the back side (a direction orthogonally crossing the crosswise direction), if calculation was conducted by substituting H=4.2 mm in the above formula (2), W became 21.5 mm; that is, the measurement-possible region was positioned inwardly by 22 mm or more from the thickness-setting member 32. In the crosswise direction, the culture liquid 10 moved back and forth (reciprocal movement) at the edge part of the pressing table 3, and the measurement values were not stable. Therefore, an experiment was conducted for a distance to the position at which the measurement value became stable, and the range was found to be positioned inwardly by 14 mm or more from the left edge part and the right edge part.

Further, the density of cells was calculated by using this pressing table 3. The density of cells was almost equal to that calculated by means of a cell counter plate.

Example 3

As shown in FIG. 9, the pressing table 3 in Example 3 differed from that in Example 1 in that a thickness-setting member 32a that had an almost square lower face was provided in a protruding manner on both ends of each thickness-setting member 32 instead of a pair of thickness-setting members 32. Other configurations were almost the same as those in Example 1.

In this pressing table 3, as for the measurement-possible region, in a direction connecting the front side and the back side (a direction orthogonally crossing the crosswise direction), if calculation was conducted by substituting H=2.1 mm in the above formula (2), W became 14.0 mm; that is, the measurement-possible region was positioned inwardly by 14 mm or more from the thickness-setting member 32a. In the crosswise direction, the culture liquid 10 moved back and forth (reciprocal movement) at the edge part of the pressing table 3, and the measurement values were not stable. Therefore, an experiment was conducted to find a distance to the position at which the measurement value became stable, and the range was found to be positioned inwardly by 5 mm or more from the left edge part and the right edge part.

Between the thickness-setting members 32a that were opposed in the crosswise direction, the measurement-possible region was positioned inwardly by a radius of 14 mm or more from the four thickness-setting members 32a. Between arcs each having a radius of 14 mm, the culture liquid 10 moved back and forth (reciprocal movement), and the measurement values were not stable. Therefore, an experiment was conducted for a distance to the position at which the measurement value became stable, the range was found to be positioned inwardly by 5 mm or more from the edge parts on the left and the right.

Further, the density of cells was calculated by using this pressing table 3. The density of cells was almost equal to that calculated by means of a cell counter plate.

Subsequently, the operation or the like of the counting device 1 with the above-mentioned configuration will be explained with reference to the drawings.

First, before measuring the number of cells in the container 11, normally, the culture liquid 10 in the container 11 was stirred. As for means for stirring the culture liquid 10, means for stirring disclosed in the above-mentioned Patent Document 1 or other stirring means can be used.

In the counting device 1, as indicated by a broken line in FIGS. 1 and 2, the lighting means 5, the imaging means 6 or the like are moved to the right side, and the pressing table 3 is in the opened state as indicated by a broken line in FIG. 3.

Subsequently, in the counting device 1, the container 11 is mounted by a measurer on the mounting table 2, and then the rotating means 35 is closed, and the closed state is kept. At this time, as shown in FIG. 4C, the thickness-setting member 32 pushes down the upper film 111 and a part of the upper film 111 that has been pushed down is brought into contact with the lower film 112. A part of the upper film 111 below the second light-passing hole 31 of the pressing table 3 is in contact with the glass plate 33. Accordingly, the thickness t of the liquid below the thickness-setting member 32 is equal to the protrusion amount H (protrusion amount H=liquid thickness t)

Here, if the thicknesses of the upper film 111 vary entirely, the thickness of a part of the upper film 111 below the thickness-setting member 32 and the thickness of a part of the upper film 111 below the second light-passing hole 31 are almost equal, the protrusion amount H becomes the liquid thickness t without being affected by the above-mentioned entire variation. Therefore, if the density of cells is calculated, the measurement accuracy can be improved.

Further, if the film thickness of the container 11 varies, the protrusion amount H becomes the liquid thickness t without being affected by difference in film thickness. Therefore, since the film thickness is not required to be taken into consideration, workability can be improved. Since no human errors occur during the adjustment of a film thickness, reliability or the like can be improved.

Further, since the pressing force of the pressing table 3 is adjusted by the compression spring 34, when the container 11 is sandwiched between the mounting table 2 and the pressing table 3, the following disadvantages can be prevented without fail; i.e. the thickness-setting member 32 presses the container 11 too strongly to damage the container 11, or the thickness-setting member 32 does not press the container 11 sufficiently, and as a result, a part of the upper film 111 of the container 11 that is pressed down by the thickness-setting member 32 is floated for a minor distance from the part of the lower film 112 of the container 11.

Further, since the second light-passing hole 31 is normally formed in the above-mentioned measurement-possible region, a disadvantage that measurement is erroneously conducted by a measurer outside the measurement-possible region can be prevented without fail.

Then, a reciprocal movement means 41 moves the lighting means 5 and the imaging means 6 above and below the second light-passing hole 31 respectively.

At this time, the protrusion amount H is set according to the type of cells, the size of the container 11, the area of the measurement-possible region, the culture period or the like.

Subsequently, the measurement-possible region is irradiated with light emitted from the lighting means 5, and then, the imaging means 6 of which the focus has been adjusted by the lifting means 42 acquires an image of cells within a range of 0.5 mm (one side) or less in the measurement-possible region.

Then, the information processing means (not shown) inputs image data from the imaging means 6, and processes acquired image data to automatically count the number of cells.

As the information processing means, a cell counting analysis apparatus, a cell counting apparatus or the like, that are known in the art, can be used.

In one or more embodiments, by using one having a specific gravity lower than that of culture cells as the culture liquid 10, culture cells are allowed to be deposited in the bottom of the container 11 and an image of these cells is acquired by placing the focus of the imaging means 6 to on the deposited cells.

As stated in the Patent Document 1 mentioned above, when the number of cells is large and cells in acquired image data (this can be referred to as the acquired image) lie on another, it is impossible to count the number of cells accurately. If the number of cells is less than a constant value, the accuracy of the density of cells obtained becomes low. In such a case, normally, by using the pressing table 3 having a different protrusion amount H, counting is conducted again.

Further, instead of changing the pressing table 3, plural (for example, three) pressing tables 3 differing in protrusion amount H and the rotating means 35 may be arranged side by side. By this configuration, instead of changing the pressing table 3, what is needed is to move the lighting means 5 and the imaging means 6 to a suitable pressing table 3, the measurement time can be shortened and workability can be improved.

When the number of cells in the measurement-possible region is measured, the density of cells can be calculated by dividing the number of cells with the volume of the measurement-possible region. Further, by multiplying the resulting density of cells with the volume of the container 11, the number of cells in the entire container 11 can be calculated.

The density of cells and the number of cells in the entire container 11 can be automatically calculated by means of an information processing means.

As mentioned above, according to the counting device 1 of one or more embodiments, if the film thickness of the container 11 varies, measurement can be conducted without taking such variations into consideration. As a result, a disadvantage that measurement accuracy is lowered can be prevented. Further, if containers differing in film thickness are used, operability and reliability can be improved since the film thickness of each container is not required to be taken into account.

In addition, since there is no need to take the liquid out of the container 11, when the liquid is culture liquid, risk of contamination can be eliminated. Further, objective data can be obtained without the skill of a measurer.

The present invention is not limited to the above-mentioned embodiments or the like, and it is needless to say various modifications are possible within the range of the present invention.

For example, in the above-mentioned embodiment, culture cells are counting objects. The counting objects are not limited thereto, and other organic substances such as plankton or inorganic substances can be counting objects. The "liquid" in the culture container also includes semi-fluid in addition to culture liquid. As culture liquid in the container 11, by using one having a specific gravity higher than the specific gravity of culture cells, culture cells are counted by allowing them to be positioned in the upper part of the container 11. Further, not only the number of cells can be counted, but also the growth state or the like of the cells can be observed.

The counting device 1 has a configuration that the pressing table 3 has the second light-passing hole 31 for lighting and the mounting table 2 has the first light-passing hole 21 for acquiring an image. The configuration is not limited thereto. For example, although not shown, the device may have a configuration in which the pressing table 3 has the second light-passing hole 31 for acquiring an image and the mounting table 2 has the first light-passing hole 21 Further, when the imaging means 6 acquires an image by utilizing reflected light, a configuration is possible in which the pressing table 3 has the second light-passing hole 31 for lighting and acquiring an image and the mounting table 2 does not have the first light-passing hole 21, or the pressing table 3 does not have the second light-passing hole 31 and the mounting table 2 has the first light-passing hole 21 for lighting and acquiring an image.

When the pressing table 3 does not have the second light-passing hole 31 and the mounting table 2 has the first light-passing hole 21 for lighting and acquiring an image, the thickness-setting member 32 on the pressing table 3 is provided such that it protrudes in such a manner it is arranged in the periphery of the first light-passing hole 21.

Further, in this case, conditions may be satisfied that the thickness-setting members 32 are provided in a protruding manner at symmetrical positions relative to a point on the pressing table 3 corresponding to the center point of the first light-passing hole 21 or a horizontal virtual central line that passes this point such that a gap is provided.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

EXPLANATION OF REFERENTIAL NUMERALS

1. Counting device
2. Mounting table
3. Pressing table
4. Casing
5. Lighting means
6. Imaging means
10. Culture liquid
11. Container
21. First light-passing hole
22. Glass plate
23. Notch
31. Second light-passing hole
32, 32a. Thickness-setting member
33. Glass plate
34. Compression spring
35. Rotating means
41. Reciprocal movement means
42. Lifting means
43. Front panel
51. Condensing lens
52. Arm member
61. Objective lens
111. Upper film
112. Lower film
351. Base part
352. Rotating plate
353. Handle
354. Third light-passing hole
411. Stage
421. Dial

What is claimed is:

1. A counting device comprising:
   a camera that acquires an image of counting objects through a light-passing hole;
   a computer that processes the image and counts a number of the counting objects;
   a flexible container comprising an upper film and a lower film;
   a mounting table;
   a pressing table arranged opposite to the mounting table; and
   one or more thickness-setting members provided on a surface of the pressing table, the surface facing the mounting table,
   wherein the counting device counts the number of the counting objects in liquid in the flexible container,
   wherein the flexible container is arranged between the pressing table and the mounting table,
   wherein the mounting table and the pressing table move relatively toward each other,
   wherein the light-passing hole is provided in at least one of the mounting table and the pressing table,
   wherein the one or more thickness-setting members protrude from the pressing table and are located in a periphery of the light-passing hole,
   wherein a protruded height of the thickness-setting member (H) and a distance between the thickness-setting member to a measurement-possible region (W) satisfy the following relationship: $W \geq -0.76 \times H^2 + 8.28 \times H$,
   wherein the protruded height is a distance from the surface of the pressing table to a protruded top of the thickness-setting member, and
   wherein the measurement-possible region is a region of the surface of the pressing table where the upper film of the flexible container contacts when the one or more thickness-setting members push down the upper film in a state that the upper film and the lower film contact each other.

2. The counting device according to claim 1, wherein the pressing table has the light-passing hole, and the one or more thickness-setting members are provided at symmetrical positions relative to a central point of the light-passing hole or a horizontally-directed virtual central line passing the central point.

3. The counting device according to claim 1, wherein the pressing table comprises a pressing force-adjusting member.

4. The counting device according to claim 1, wherein the height of the one or more thickness-setting members is adjustable.

5. The counting device according to claim 1, wherein the container is a culture container and the counting objects are cells.

* * * * *